United States Patent
Pascaloff et al.

(10) Patent No.: US 6,638,290 B2
(45) Date of Patent: Oct. 28, 2003

(54) CONNECTOR ASSEMBLY FOR A SURGICAL TOOL

(75) Inventors: John Pascaloff, Keswick, VA (US); Joseph Ventura, Ruckersville, VA (US)

(73) Assignee: Microaire Surgical Instruments, Inc., Charlottesville, VA (US)

( * ) Notice: Subject to any disclaimer, the term of this patent is extended or adjusted under 35 U.S.C. 154(b) by 442 days.

(21) Appl. No.: 09/729,767

(22) Filed: Dec. 6, 2000

(65) Prior Publication Data

US 2002/0068952 A1 Jun. 6, 2002

(51) Int. Cl.[7] ................................................ A61B 17/14
(52) U.S. Cl. ............................ 606/177; 30/337; 279/48
(58) Field of Search ........................... 30/329, 337, 339, 30/338, 522; 279/48, 47, 46.1, 90; 606/177, 178, 179, 176, 82, 522

(56) References Cited

U.S. PATENT DOCUMENTS

| | | | | |
|---|---|---|---|---|
| 4,020,555 A | * | 5/1977 | Hedrick | 30/392 |
| 4,626,146 A | * | 12/1986 | Neumaier | 408/239 R |
| 4,691,929 A | * | 9/1987 | Neumaier et al. | 279/19.3 |
| 5,306,025 A | * | 4/1994 | Langhoff | 279/90 |
| 5,340,129 A | * | 8/1994 | Wright | 279/90 |
| 5,433,457 A | * | 7/1995 | Wright | 279/90 |
| 5,575,071 A | * | 11/1996 | Phillips et al. | 30/392 |
| 5,609,603 A | * | 3/1997 | Linden | 606/177 |
| 5,916,218 A | * | 6/1999 | Hagen et al. | 606/82 |
| 5,996,452 A | * | 12/1999 | Chiang | 81/429 |
| 6,113,619 A | * | 9/2000 | Pascaloff | 606/178 |
| 6,209,208 B1 | * | 4/2001 | Marinkovich et al. | 30/392 |
| 6,302,406 B1 | * | 10/2001 | Ventura | 279/48 |

\* cited by examiner

*Primary Examiner*—Danny Worrell
(74) *Attorney, Agent, or Firm*—McGuireWoods LLP

(57) ABSTRACT

A connector assembly for connecting a surgical saw blade to a housing of a surgical instrument. The connector assembly allows a surgeon to align, insert and lock the surgical blade in the collect of the surgical instrument without any special tools, and further provides a stable and robust platform for mounting the surgical saw blade thereto. The connector assembly includes a gripper having a centrally located bore and a pair of opposing shelves. A shaft having shoulders is slidably fitted within the bore of the gripper. The shoulders communicate with ledges of the shelves to prohibit movement of the finger gripper. This same mechanism also prevents movement of a surgical saw blade, once inserted within the slot of the shaft, from becoming dislodged or ejected from the connector assembly. A biasing spring biases the gripper in a first position, but the gripper can move between the first position and a second position.

41 Claims, 6 Drawing Sheets

CONNECTOR ASSEMBLY FOR A SURGICAL TOOL

BACKGROUND OF THE INVENTION

1. Field of the Invention

The present invention relates generally to a connector assembly for a surgical instrument and, more particularly, to a connector assembly for securing a surgical tool to a housing of a surgical instrument.

2. Background Description

Connector assemblies in surgical instruments play an important role in the efficacy and safety of the surgical instrument. That is, a surgical instrument will not be deemed safe and effective without a connector assembly which can properly secure the surgical tool to the housing of the surgical instrument. It is with this in mind that manufacturers of surgical instruments give the utmost attention and care to the design and manufacture of connector assemblies.

Connector assemblies are typically referred to as collets and are designed to lock the surgical tool within the housing of the surgical instrument. Although many collets are currently manufactured and sold worldwide for use in surgical instruments, there is certainly concern that many of these collets do not maintain a secure connection between the surgical tool and the housing of the surgical instrument over extended periods of time. It is also noted that many of these collets can only secure a surgical tool to the housing with cumbersome tools, which have a tendency of breaking or being lost. In any of these scenarios, the surgical instrument may be rendered useless, thus requiring the disposal of the surgical instrument.

By way of explanation, in order to mount and secure a surgical tool such as a surgical saw blade within a housing of the surgical instrument it is necessary to place the surgical saw blade into the collet of the surgical instrument. Thereafter, the collet is rotated by a key or a special tool so as to press fit (e.g., friction fit) the surgical saw blade between opposing arms of the collet. However, these type of collets have a tendency to become "stripped" during the mounting of or removal of the surgical saw blade. This may pose a severe safety risk to the patient, especially if the surgical saw blade breaks or becomes worn and cannot be removed during a surgical procedure. In the cases when the collet becomes stripped or otherwise rendered inoperable, the surgical instrument must either be discarded or retrofitted with a new collet.

A further shortcoming of press or friction fitting the surgical tool within the collet of the surgical instrument is the fact that the surgical tool can easily become dislodged or loosened during the surgical procedure. This typically happens due to the reciprocating or rotational movement of the surgical tool during the surgical procedure. The loosening or dislodgement of the surgical tool may also be the result of an overused or deteriorated collet, or simply due to the force applied by the surgeon on the surgical instrument during the surgical procedure. Regardless of cause, such loosening or dislodgement of the surgical tool from the surgical instrument certainly poses a serious risk to the patient during a surgical procedure.

Spring loaded chucking systems used in surgical instruments are also well known in the medical field. However, the design of these type of spring loaded systems permit the surgical saw blade to be accidently ejected therefrom; that is, these spring loaded systems have a tendency to permit the surgeon to accidently "hit" the spring loaded release mechanism during use thereof. In this case, the surgical tool will spontaneously eject from the surgical instrument posing serious injury to both the surgeon and the patient.

What is thus needed is a connector assembly that is easy to use and which securely mounts and locks the surgical tool within the housing of the surgical instrument. Such an assembly would preferably be a keyless system.

SUMMARY OF THE INVENTION

It is therefore an object of the present invention to provide a connector assembly which overcomes the above shortcomings.

It is another object of the present invention to provide a connector assembly which securely connects and locks a surgical tool within a housing of a surgical instrument.

It is a further object of the present invention to provide a connector assembly which properly aligns the surgical tool within the housing of the surgical instrument.

It is still a further object of the present invention to provide a connector assembly which securely locks the surgical tool within the housing of the surgical instrument without any special tools, equipment and the like.

It is also a further object of the present invention to provide a connector assembly which allows a surgeon to easily remove and replace the surgical tool during a surgical procedure.

In one aspect of the invention, a connector assembly is provided for connecting a surgical tool to a surgical instrument. The connector assembly has a gripper having a centrally located bore and opposing shelves formed in the centrally located bore. The opposing shelves form an elongated slot therebetween. A shaft having a longitudinal slot and adjacent sections having predetermined cross sections is slidably located within the central bore. The predetermined cross sections of the shaft prohibit movement of the shaft when the gripper is in a first position. A biasing spring mates with the gripper and the shaft.

In another aspect of the invention, a connector assembly has a collet with a first section, a second section and a third section. A first shoulder is formed between the first section and the second section and a second shoulder is formed between the second section and the third section. A slot extends along a length of the collet to the third section. A gripper having a centrally located bore is rotable about the collet. The shoulder and the opposing shoulder are aligned over opposing ledges of shelves located within the bore of the gripper when the gripper is biased in a first position.

In yet another embodiment, a surgical instrument is provided with a connector assembly. The surgical instrument includes a motor positioned within a housing. A collet is pivotally connected to the motor. The collet is used for connecting a surgical tool to the surgical instrument. The connector assembly includes the collet in addition to a gripper having a centrally located bore. Shelves are formed in the centrally located bore of the gripper which form an elongated slot within the bore of the gripper. The collet includes a longitudinal slot as well as a first section, a second section and a third section. The second section has a different cross section than either of the first section and the second section. A first and second shoulder are formed between the first, second and third sections. The shoulders prevent movement of the gripper when the gripper is biased in a first position.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENT OF THE INVENTION

The present invention is directed to a connector assembly for connecting a surgical saw blade to a housing of a surgical instrument. The connector assembly is a keyless system and is capable of connecting several types of surgical saw blades including, for example, a sternum surgical saw blade, to the housing of the surgical instrument. By using the connector assembly of the present invention, a surgeon or other medical personnel can easily align, insert and lock the surgical blade in the connector assembly of the surgical instrument without any special tools, equipment and the like. This enables the surgeon or other medical personnel to easily remove and replace the surgical saw blade during a surgical procedure. The connector assembly of the present invention also provides a stable and robust platform for mounting of the surgical saw blade, while ensuring that the surgical saw blade will remain firmly secured within the housing of the surgical instrument during a surgical procedure.

Connector Assembly

Figure 1:
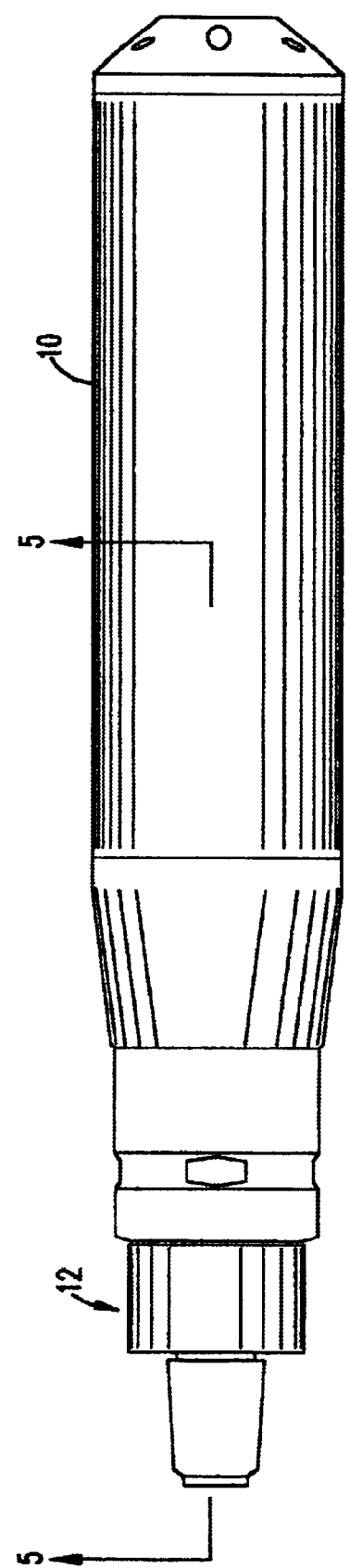
FIG. 1 shows a plan view of a surgical instrument using a connector assembly of the present invention.

Referring now to the drawings, and more particularly to FIG. 1, there is shown a plan view of a surgical instrument using a connector assembly of the present invention. More particularly, the surgical instrument includes a housing 10 which houses a motor or other driving device such as, for example, a reciprocating drive mechanism. The housing 10 is illustrated as a wand-type housing; however, other types of housings such as a pistol grip type housing are also contemplated for use with the present invention. A portion of the connector assembly, generally depicted as reference numeral 12, extends from a distal end of the housing 10. The connector assembly 12 is further described in more detail with reference to FIGS. 3–7. Speed controls (not shown) may also be provided on the housing 10.

Figure 2:
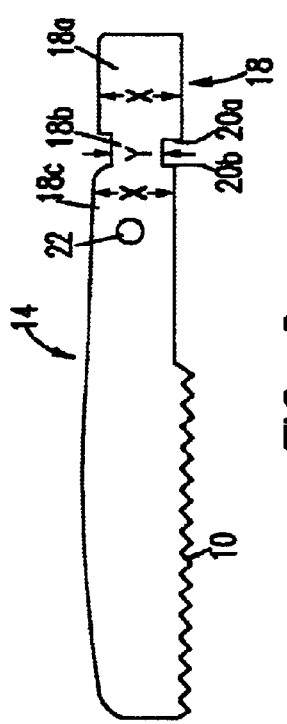
FIG. 2 shows a surgical tool used with the connector assembly of the present invention.

FIG. 2 shows a surgical tool used with the connector assembly 12 of the present invention. The surgical tool is depicted as reference numeral 14 and is preferably a surgical saw blade; however, other surgical tools may also be used with the present invention such as a screw driver and the like. The surgical saw blade 14 includes a toothed portion 16 and a shank portion 18. The shank portion 18 has three sections, a distal section 18a, a middle section 18b and a proximal section 18c. In one embodiment, the distal and proximal sections 18a and 18c have substantially a same cross section "X", while the middle section 18b has a smaller cross section "Y". This arrangement forms opposing shoulders 20a and 20b between the distal and proximal sections 18a and 18c. It is further contemplated by the present invention that the distal section 18a is not limited to the cross section "X" (e.g., the same cross section as the proximal section 18c), but may also have a cross section which is larger or smaller than the cross section of the proximal section 18c. It is preferred, however, that a shoulders remain between the distal and proximal sections 18a and 18c. In embodiments, an aperture 22 may be formed in the distal section 18c of the shank 18.

Figure 3:
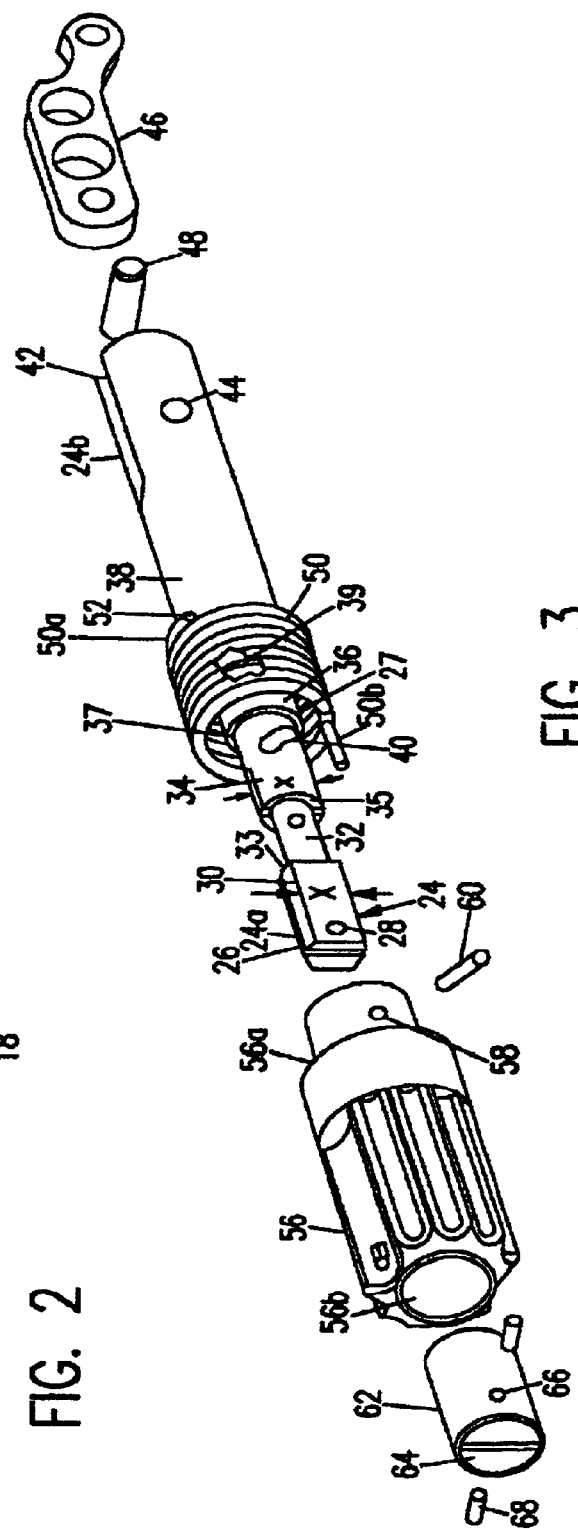
FIG. 3 shows an exploded perspective view of the connector assembly of the present invention.

FIG. 3 shows an exploded perspective view of the connector assembly 12 of the present invention. As seen in this view, the connector assembly 12 includes a quick release collet 24 having a first end 24a and a second end 24b. A first longitudinal slot 26, which accommodates the shank 18 of the surgical tool 14, is provided at the first end 24a of the quick release collet 24. A pair of flat sections 30 are provided at the first end 24a of the quick release collet 24. The flat sections 30 preferably have a cross section "X" which corresponds to the cross section "X" of the proximal section 18c of the surgical tool 14. It should be well understood by those of ordinary skill in the art that the flat sections 30 may also have a different cross section than that of the proximal section 18c of the surgical tool 14. A pair of apertures 28 are provided respectively in the pair of flat sections 30, and during operation of the surgical instrument may be aligned with the aperture 22 of the surgical tool 14.

Still referring to FIG. 2, the quick release collet 24 further includes four adjacent sections 32, 34, 36 and 38 each of a different cross section. In the preferred embodiment, each of these four sections are cylindrically shaped and thus each have a different circumference, but it should be understood that other shapes may also be used with the present invention. Being more specific, the first section 32 has a first circumference which is smaller than the cross section of the flat sections 30. The circumference of the first section 32 forms a shoulder 33 between the first section 32 and the flat sections 30. The second section 34 has a second circumference preferably larger than the first circumference of the first section 32. The third section 36 has a third circumference preferably larger than the circumference of the second section 34. Similarly, the fourth section 38 has a fourth circumference preferably larger than the circumference of the third section 36. In this configuration, shoulders 35, 37 and 39, respectively, are thus formed between the remaining sections 32, 34 and 36.

In one embodiment of the present invention, the cross section "X" of the flat sections 30 is not only substantially equal to the cross section of the proximal section 18c of the shank 18, but also is substantially equal to the cross section (e.g., diameter) of the second section 24 of the quick release collet 24. Additionally, the cross section of the first section 32 of the quick release collet 24 may be substantially equal to the cross section "Y" of the middle section 18b of the shank 18. In this manner, the sections 18a, 18b and 18c of the shank 18 will correspond in size to the flat sections 30, the first section 32 and the second section 34, respectively, of the quick release collet 24. In another embodiment of the present invention, the cross section of the flat sections 30 is different than that of the second section 24; however, a shoulder 33 should always exist between the flat sections 30 and the first section 32.

It is further contemplated by the present invention that the longitudinal slot 26 of the quick release collet 24 extends to a point approximately midway through the second section 34 of the quick release collet 24. This forms a "stop" mechanism which limits the insertion distance of the shank 18 thus ensuring a proper alignment with the shoulders 20a and 20b of the shank 18 and the shoulders 33 and 35 of the quick release collet 24. Note that these shoulders do not have to be in exact alignment for the invention to function in the intended manner, but such alignment merely provides a basic guide to ensure that the surgical tool 14 can be properly and readily locked to the housing 12 of the surgical instrument.

Figure 6:
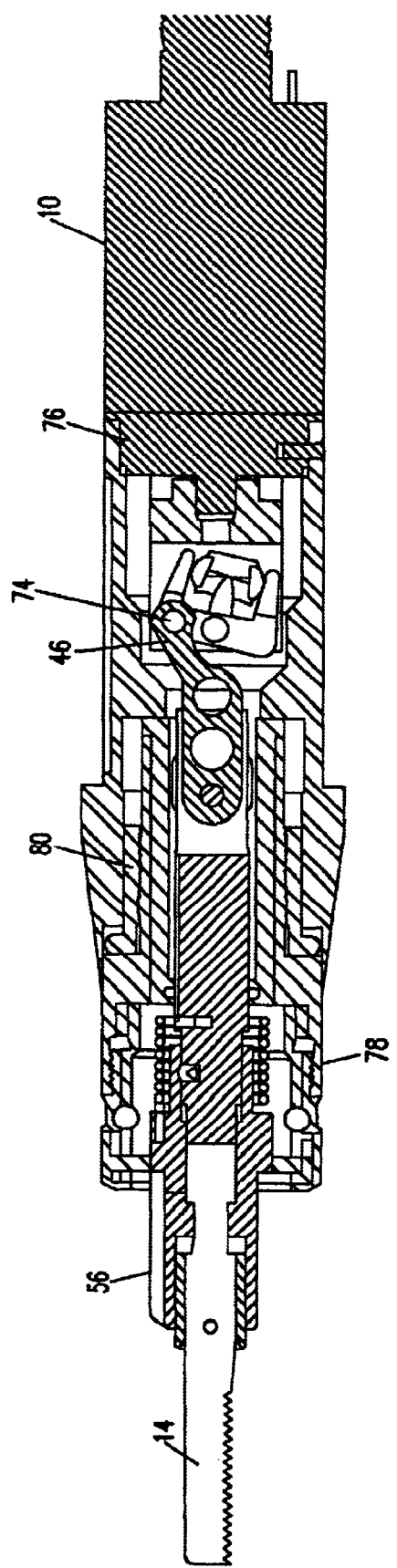
FIG. 6 shows a cut-away view of the surgical instrument of FIG. 1 along line 6—6.

FIG. 3 further shows a cam follower 40 formed in the second section 34 of the quick release collet 24, and an end slot 42 located at the second end 24b of the quick release collet 24. A connecting aperture 44 extends through the end slot 42 and a motor connecting arm 46 is pivotally connected within the end slot 42 via a pin 48. The connecting arm 46 is coupled to the motor via a reciprocating motor assembly (FIG. 6).

Referring still to FIG. 3, a torsion spring 50 is positioned about the outer circumference of the third and fourth sections 36 and 38 of the quick release collet 24. The inner circumference of the torsion spring 50 is preferably larger than the circumference of the fourth section 38 of the quick release collet 24. A first end 50a of the torsion spring 50 mates with a bore 52 formed in the third section 38 of the quick release collet 24 and a second end 50b of the torsion spring 50 mates with a through hole 54 formed in a finger gripper 56. The torsion spring 50 may be isolated to the third section 36, in embodiments.

The finger gripper 56 includes a first end 56a having an outer circumference that is slightly smaller than the inner circumference of the torsion spring 50. An inner circumference of the first end 56a is substantially a same size (slightly larger) as the outer circumference of the third section 36 of the quick release collet 24. The finger gripper 56 further has a second end 56b which has an inner circumference that is larger than the inner circumference of the first end 56a. A through hole 58 is formed in the first end 56a of the finger gripper 56, and a cam pin 60 is inserted within the through hole 58 which, in operation, communicates with the cam follower 40. By using the torsion spring 50 and the cam mechanism arrangement, the finger gripper 56 is biased toward a first direction (e.g., toward the slot 42 of the quick release collet 24), but is capable of being rotated and simultaneously moved in a second direction equal to a travel of the cam follower 40. After insertion or removal of the surgical tool 14, the finger gripper 56 will automatically move toward the first direction and return to an original position via the biasing force of the torsion spring 50.

FIG. 3 also shows a nose portion 62 inserted within the inner circumference of the second end 56b of the finger gripper 56. The nose portion 62 has a slot 64 which is aligned with the longitudinal slot 26 of the quick release collet 24. This alignment allows the shank 18 of the surgical tool 14 to pass smoothly through the slots of the quick release collar 24 and the nose portion 62 to the "stop" position. A pair of apertures 66 are provided in each side of the nose portion 62 and correspond to the apertures 28 of the quick release collet 24. In the assembled arrangement, a pair of pins 66 extend through the apertures 64 of the nose portion 62 and mate with the respective apertures 28 of the quick release collet 24 thus ensuring that the nose portion 62 remains coupled to the quick release collet 24. The nose portion 62 preferably extends outward from the second end 56b of the finger gripper 56.

Figure 4:
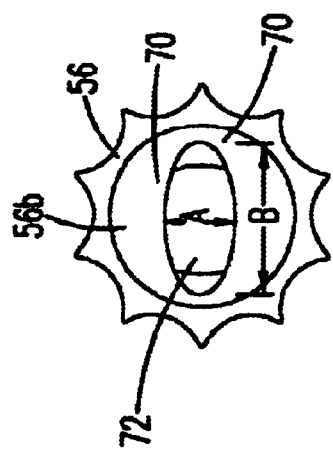
FIG. 4 shows a side plan view of a gripper used with the connector assembly of the present invention.

FIG. 4 shows a side view of the finger gripper 56 from the second end 56b. A pair of shelves 70 (having ledges) are positioned within the second end 56b of the finger gripper 56. The shelves 70 form an elongated slot 72, where the elongated slot may be an oval slot or other shape having a non uniform cross section about an axis orthogonal to the elongated portion of formed by the shelves 70. The shelves 70 each have a depth slightly larger than the middle section 18b of the shank 18; that is, the depth or thickness of the shelves 70 is slightly larger than the area between the proximal and distal sections 18a and 18c of the surgical tool 14. Also, a distance represented as "A" spanning the narrow space between the shelves 70 is smaller than the cross section of both the proximal and distal sections 18a and 18c but larger than the cross section of the middle portion 18b of the surgical tool 14. A distance represented as "B" spanning the lengthwise space of the shelves 70 is larger than the cross section of both the proximal and distal sections 18a and 18c of the surgical tool 14. In this arrangement, the finger gripper 56 is capable of properly aligning and locking the surgical instrument within the quick release collet 24 of the present invention. A discussion of the particular operation of the quick release collet 24 will be discussed below.

Figure 5:
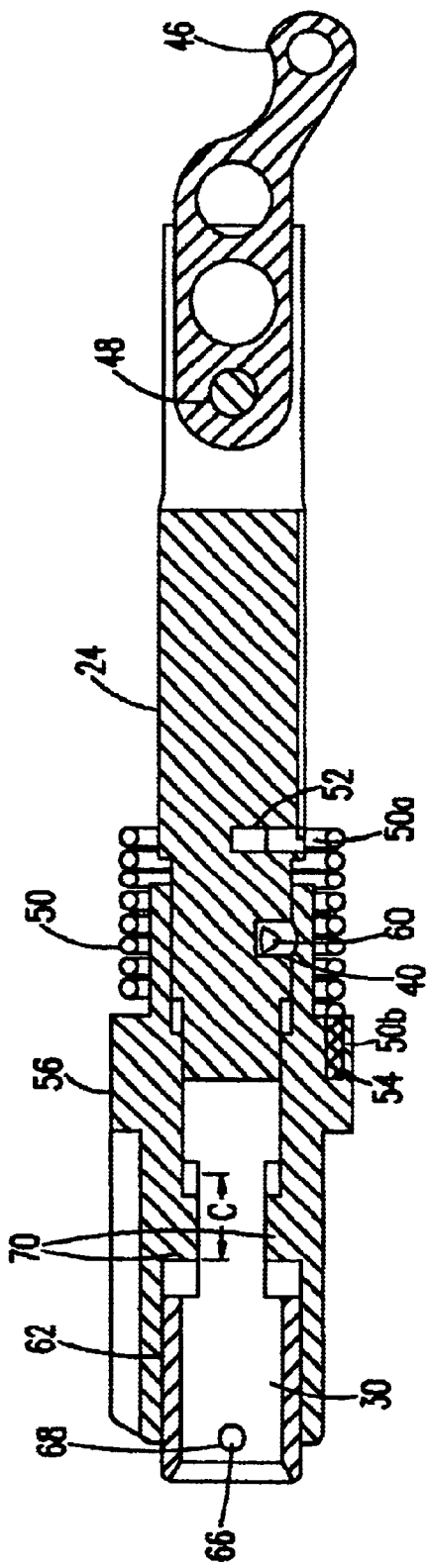
FIG. 5 shows a cut-away view of the assembled connector assembly of FIG. 1.

FIG. 5 shows a cross section of the assembled connector assembly of the present invention. In particular, the finger gripper 56 is rotatably coupled to the quick release collet 24 via the torsion spring 50 and the cam mechanism. The first end 52a of the torsion spring 50 mates with the bore 52 formed in the quick release collet 24 and the second end 50b of the torsion spring 50 mates with the through hole 54 formed in the finger gripper 56. The torsion spring 50 biases the finger gripper 56 in the first direction toward the motor connecting arm 46. The nose portion 62 extends outward from the finger gripper 56, and includes the aperture 66 and pin 68 inserted therein. The nose portion 62 substantially surrounds the flat sections 34 of the quick release collet 24.

As further seen in FIG. 5, the shelves 70 of the finger gripper 56 have a certain thickness or depth (represented by "C"). In the preferred embodiment, the thickness "C" is smaller than both the first section 32 of the quick release collet 24 and the middle section 18b of the surgical tool 14. FIG. 5 also shows the cam pin 60 inserted within the through hole 58 which, in operation, communicates with the cam follower 40.

FIG. 6 shows a cut-away view of the surgical instrument along line 6—6 of FIG. 1. The view of FIG. 6 demonstrates the mechanism for attaching the motor connecting arm 46 to the motor as well as maintaining the connector assembly 12 securely within the housing 10. The motor connecting arm 46 is pivotally coupled to the reciprocating motor assembly 74 which, in turn, is coupled to the motor 76. The motor is housed within a compartment of the housing 10. The connector assembly 12 is securely mounted to the housing 10 via a threaded housing connector assembly 78. The threaded housing connector assembly 78 includes a press fit collar 80 which is positioned between the threaded housing connector 78 which fits into the housing 10.

Figure 7:
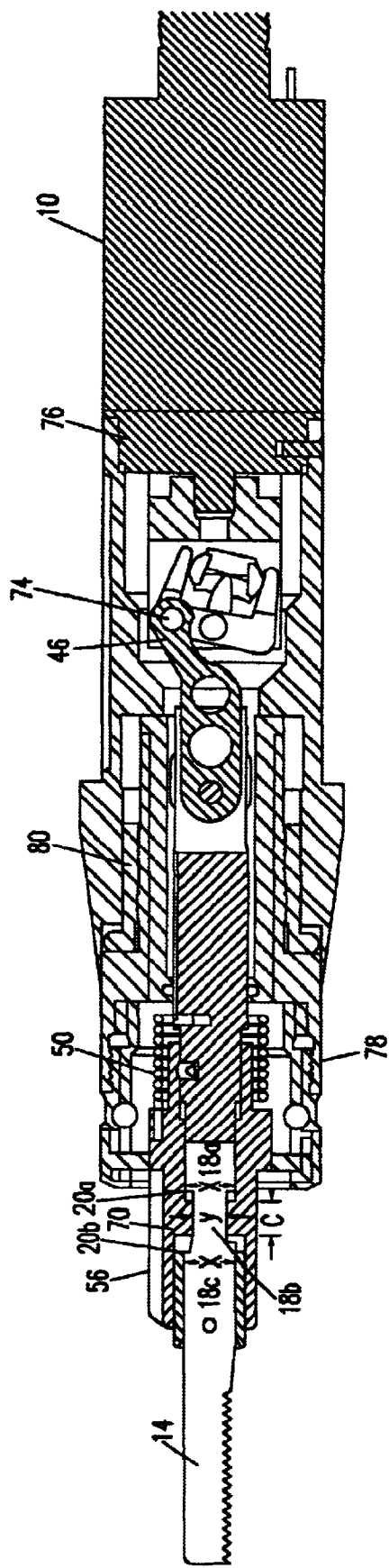
FIG. 7 shows a cut-away view of the surgical instrument of FIG. 1 along line 6—6 with a surgical tool inserted within the connector assembly of the present invention.

FIG. 7 shows a cut-away view of the surgical instrument using the connector assembly of FIG. 1 along line 6—6 with the surgical tool inserted therein. In the assembled form with the surgical tool 14 inserted within the longitudinal slot 26 of the quick release collet 24 and the slot 64 of the nose portion 62, the shoulder 20a formed between the distal section 18a and the middle section 18b of the surgical tool 14 is positioned over the ledge of the shelves 70. The finger gripper 56 is biased toward the motor connecting arm 46 via the torsion spring 50 maintaining the surgical tool 14 in a locked position.

Method of Inserting the Surgical Tool into the Connector Assembly

Figure 8:
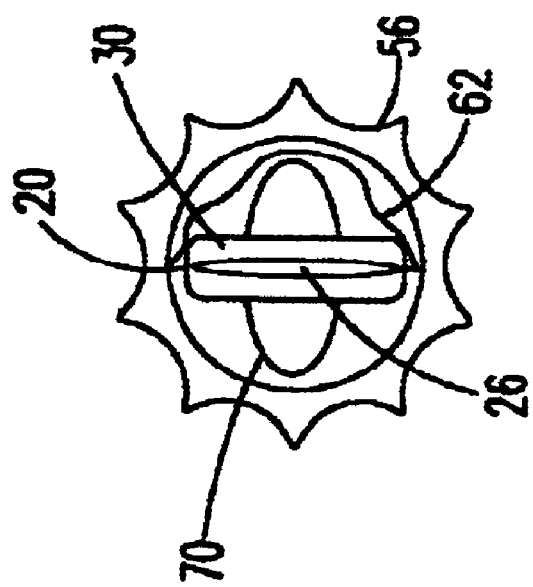
FIG. 8 shows a side view of the connector assembling when the gripper is in a biased position.

Prior to inserting the surgical tool 14 into the connector assembly 12 of the present invention, the finger gripper 56 remains in a biased position (toward the first direction) due to the forces exerted by the torsion spring 50. In this biased position, the shoulder 33 between the flat sections 30 and the first section 32 of the quick release collet 24 will be prohibited from passing through the slot 72 formed in the finger gripper 56 (FIG. 8). As will be discussed below, when the surgical tool 14 is thus inserted within the slots of the nose portion 62 and the quick release collar 24, the shoulders 20a and 20b will be positioned on opposing sides of the shelves 70 thus prohibiting the lateral movement of the surgical tool 14 within the connector assembly 12. In other words, the surgical tool 14 will be locked firmly within the connector assembly.

Figure 9:
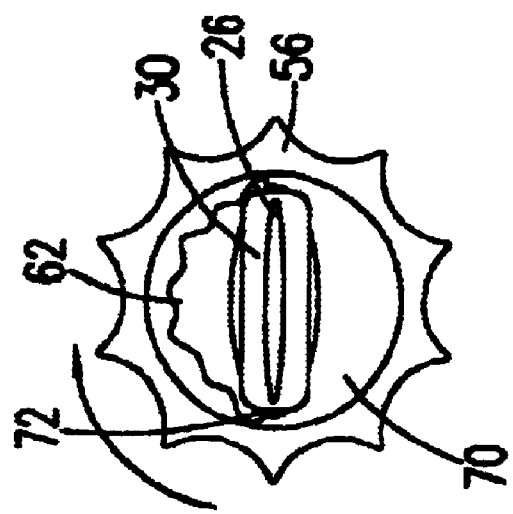
FIG. 9 shows a side view of the connector assembly when the gripper is rotated.

To insert the surgical tool 14 into the connector assembly 12, the finger gripper 56 is rotated preferably counter-clockwise. During the rotation of the finger gripper 56, the pin 60 will travel within the cam follower 40. This will move the finger gripper 56 towards a front portion of the surgical instrument housing 10. As the finger gripper rotates, the flat portions 30 and more particularly the longitudinal slot 26 of the quick release collet 24 (and the slot 64 of the nose portion 62) align with the slot 72 (along the elongated direction of the slot) of the finger gripper 56 (FIG. 9). At this stage, the shaft 18 of the surgical blade or tool may be smoothly inserted within the slot 64 of the nose portion 62 and the longitudinal slot 26 of the quick release collet 24. The distance of insertion of the shaft 18 of the surgical tool 14 will be limited due to the "stop" mechanism of the quick release collet 24. In this position of the surgical tool 14, the shoulders 20a and 20b of the shank 18 will be aligned with the shoulders 33 and 35 of the quick release collet 24. Also, in this position, the middle portion 18b will be positioned between the opposing ledges of the shelves 70.

Once the surgical tool 14 is inserted, the operator will release the finger gripper 56 which will then automatically move to the biased position. In this position, the finger gripper 56 has also rotated to the position of FIG. 8. In the position of FIG. 8, the shoulders 20a and 20b of the shank 18 will be positioned over opposing sides of the shelves 70 thus prohibiting movement of the surgical tool 14. This position will thus lock the surgical tool 14 within the connector assembly of the present invention. Removal of the surgical tool 14 can be performed by reversing the above steps.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A connector assembly for connecting a surgical tool to a surgical instrument, the connector assembly comprising:
   a gripper having a centrally located bore;
   opposing shelves formed in the centrally located bore of the gripper, the opposing shelves forming an elongated slot within the bore;
   a shaft having a longitudinal slot along a length thereof and adjacent sections having predetermined cross sections, the predetermined cross sections prohibiting movement of the shaft when the gripper is in a first position; and
   a biasing spring mating with the gripper and the shaft, the biasing spring biasing the gripper in the first position.

2. The connector assembly of claim 1, wherein the gripper is rotatable between the first position and a second position remote from the first position.

3. The connector assembly of claim 1, further comprising a cam follower formed in the shaft, the cam follower having a first end of travel corresponding to the first position and a second end of travel corresponding to a second position remote from the first position.

4. The connector assembly of claim 3, further comprising:
   a side through hole formed within the gripper, the side bore corresponding to the cam follower; and
   a pin positioned through the side through hole of the gripper and communicating with the cam follower, wherein
      the biasing spring biases the gripper towards the first end of travel of the cam follower corresponding to the first position, and
      the gripper is capable of rotating about the shaft and moving along a length of the shaft by traveling along the travel of the cam follower between the first position and the second position.

5. The connector assembly of claim 1, wherein the adjacent sections are at least three adjacent sections.

6. The connector assembly of claim 5, further comprising a stop mechanism in a third section of the at least three adjacent sections, wherein the longitudinal slot extends to the stop mechanism.

7. The connector assembly of claim 5, wherein a shoulder is formed between a first of the three adjacent sections and an adjacent section of the three adjacent sections.

8. The connector assembly of claim 7, wherein the shoulder prohibits the movement of the shaft when the gripper is in the first position.

9. The connector assembly of claim 7, wherein an opposing shoulder is formed between a third section of the three adjacent sections and the adjacent section.

10. The connector assembly of claim 9, wherein the shoulder and the opposing shoulder are positioned over ledges of the shelves when the gripper is in the first position thereby locking movement of the gripper.

11. The connector assembly of claim 9, wherein the adjacent section of the three adjacent sections has a cross section different than the first and the third sections of the three adjacent sections.

12. The connector assembly of claim 9, wherein the adjacent section of the three adjacent sections and the third section of the three adjacent sections have a different circumference.

13. The connector assembly of claim 1, wherein the adjacent sections are at least five adjacent sections each having a shoulder formed therebetween.

14. The connector assembly of claim 13, wherein at least four of the at least five adjacent sections each have a different cross section.

15. The connector assembly of claim 13, wherein at least two of the at least five adjacent sections have a substantially same cross section.

16. The connector assembly of claim 13, wherein at least four of the at least five adjacent sections have a different circumference.

17. The connector assembly of claim 16, wherein each circumference of the different circumference becomes progressively larger in a stepped fashion.

18. The connector assembly of claim 1, further comprising opposing shoulders formed between sections of the adjacent sections, wherein the opposing shoulders substantially become aligned with a longitudinal axis of the elongated slot as the gripper moves between the first position and a second position remote from the first position.

19. The connector assembly of claim 1, wherein the longitudinal slot of the shaft is substantially orthogonal with a longitudinal axis of the elongated slot when the gripper is in the first position.

20. The connector assembly of claim 1, wherein
the shaft includes four adjacent sections,
a shoulder is formed between each adjacent section, and
the shoulder formed between a first section and a second section and the shoulder formed between a third section and a fourth section of the four adjacent sections are positioned over opposing ledges of the shelves when the gripper is in the first position thereby locking the motion of the gripper.

21. A connector assembly, comprising:
a collet having a first section, a second section and a third section;
a first shoulder being formed between the first section and the second section;
a second shoulder being formed between the second section and the third section;
a slot extending partially along a length of the collet;
a gripper having a centrally located bore, the gripper being rotable about the collet;
a pair of shelves located within the centrally located bore of the gripper, the shoulder and the second shoulder being aligned over opposing ledges of each of the shelves when the gripper is biased in a first position.

22. The connector assembly of claim 21, further comprising an elongated slot formed between the shelves, the slot of the collet being orthogonal to a longitudinal axis of the elongated slot when the gripper is in the first position.

23. The connector assembly of claim 22, wherein the slot of the collet is substantially parallel with the longitudinal axis of the elongated slot as the gripper is rotated toward a second position from the first position.

24. The connector assembly of claim 21, further comprising a cam mechanism, the cam mechanism allows the gripper to move and rotate between the first position and a second remote position about the collet.

25. The connector assembly of claim 24, further comprising a biasing spring connected between the gripper and the collet, the biasing spring biasing the gripper in the first position.

26. The collet assembly of claim 21, further comprising a nose portion positioned partially about the collet and within the centrally located bore of the gripper, the nose portion having a slot which is aligned with the slot of the collet.

27. The connector assembly of claim 21, wherein a terminal portion of the slot of the collet is a stop mechanism.

28. The connector assembly of claim 21, wherein the gripper includes a first end and a second end, each having a different inner circumference.

29. The connector assembly of claim 21, further comprising a connecting arm pivotally coupled to the collet at an end remote from the slot.

30. A surgical instrument, comprising:
a housing;
a motor positioned within the housing;
a collet pivotally connected to a motor connecting arm, the collet including a connector assembly for connecting a surgical tool to the collet, the connecting assembly including:
a gripper having a centrally located bore, the gripper further having a first section, a second section and a third section, the second section having a different cross section than either of the first section and the second section;
opposing shelves formed in the centrally located bore of the gripper, the opposing shelves forming an elongated slot within the bore;
a longitudinal slot formed along a length of the collet;
a shoulder formed between the first section and the second section;
an opposing shoulder formed between the second section and the third section,
wherein the shoulder and the opposing shoulder prevent movement of a surgical tool when the gripper is biased in a first position.

31. The surgical instrument of claim 30, wherein the longitudinal slot of the collet is orthogonal to a longitudinal axis of the elongated slot when the gripper is in the first position.

32. The surgical instrument of claim 31, wherein the longitudinal slot of the collet is substantially parallel with the longitudinal axis of the elongated slot as the gripper is rotated toward a second position from the first position.

33. The surgical instrument of claim 30, further comprising a cam mechanism which allows the gripper to rotate between the first position and a second remote position about the collet.

34. The surgical instrument of claim 30, further comprising a biasing spring connected between the gripper and the collet, the biasing spring biasing the gripper in the first position.

35. The collet assembly of claim 30, further comprising a nose portion positioned partially about the collet and within the centrally located bore of the gripper, the nose portion having a slot aligned with the slot of the collet.

36. The surgical instrument of claim 30, wherein a terminal portion of the slot of the collet and a step pin associated with the collet is a stop mechanism.

37. The surgical instrument of claim 30, further comprising a connecting arm assembly pivotally coupled between the collet and the motor connecting arm.

38. The surgical instrument of claim 30, further comprising a surgical tool having a shaft coupled to the collet.

39. The surgical instrument of claim 38, wherein:
the surgical tool has a first section, a second section and a third section, the second section having a different cross section than either of the first section and the second section;
a shoulder formed between the first section and the second section;
an opposing shoulder formed between the second section and the third section,
wherein the shoulder and the opposing shoulder of the surgical tool are positioned on opposing sides of the shelves of the gripper such that when the gripper is in the first position the shoulder and the opposing shoulder of the surgical tool are positioned over the shelves thus preventing the movement of the surgical tool within the slot of the collet.

40. The surgical instrument of claim 39, wherein the first section, the second section and the third section of both the surgical tool and the collet have substantially same cross sections.

41. The surgical instrument of claim 39, wherein the shoulder and the opposing shoulder of the surgical tool are positioned on opposing sides of the shelves of the gripper such that when the gripper is in a second position remote from the first position the shoulder and the opposing shoulder of the surgical tool align within the elongated slot of the gripper thereby allowing the surgical tool to be removed from the collet.

* * * * *